United States Patent [19]

Sawaragi et al.

[11] Patent Number: 4,847,397

[45] Date of Patent: Jul. 11, 1989

[54] METHOD FOR THE PRODUCTION OF SILYL GROUP CONTAINING AMINE COMPOUNDS

[75] Inventors: Fujio Sawaragi, Chigasaki; Hiroo Taniguchi, Hadano, both of Japan

[73] Assignee: Dow Corning Kabushiki Kaisha, Tokyo, Japan

[21] Appl. No.: 194,746

[22] Filed: May 17, 1988

[30] Foreign Application Priority Data

May 26, 1987 [JP] Japan .................................. 62-127056

[51] Int. Cl.$^4$ .............................................. C07F 7/10
[52] U.S. Cl. .................................................... 556/418
[58] Field of Search ........................................ 556/418

[56] References Cited

U.S. PATENT DOCUMENTS

| | | | |
|---|---|---|---|
| 2,774,778 | 12/1956 | Sommer | 556/418 |
| 3,458,556 | 7/1969 | Di Paola | 556/418 |
| 4,554,369 | 11/1985 | Hill et al. | 556/418 |
| 4,562,278 | 12/1985 | Hill | 556/418 |

*Primary Examiner*—Paul F. Shaver
*Attorney, Agent, or Firm*—Jim L. DeCesare

[57] ABSTRACT

A method of preparing silyl group containing carboxylic acid type amphoteric surfactants in which a hydrocarbon substituted amine compound (1) is reacted with a silane compound (2) to produce a reaction product having at least one amino or imino group in the molecule. The reaction product of (1) and (2) is in turn reacted with a functionalized carboxylic acid to produce the desired amphoteric surfactant material.

7 Claims, No Drawings

METHOD FOR THE PRODUCTION OF SILYL GROUP CONTAINING AMINE COMPOUNDS

BACKGROUND OF THE INVENTION

The present invention relates to a method for the production of novel silyl group-containing amine compounds, and more specifically relates to a method for the production of silyl group-containing carboxylic acid-type amphoteric surfactants.

Various types of amphoteric surfactants with various molecular structures are known in the art and are used in a number of fields; however, the development of amphoteric surfactants, with their special properties, has continued with the goal of achieving the effective industrial utilization of their properties such as solubilizability, emusulsifiability, wettability, detergency etc., as well as those properties of amphoteric surfactants which cannot be found in ionic and nonionic surfactants, for example, low toxicity, excellent hard-water resistance, and good mixability with other surfactants.

SUMMARY OF THE INVENTION

The present invention was achieved as a consequence of such research and development, and has as its object the introduction of a method for the production of novel silyl group-containing amine compounds which have a high affinity for various substrates.

The distinctive feature of the present invention's method for the production of silyl group-containing amine compounds is that (a) a hydrocarbon-substituted amine compound having the following formula (1)

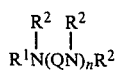

(in formula (1), $R^1$ is a monovalent hydrocarbon group; one of the three groups $R^2$ is a hydrogen atom while the other two, which may be the same or may differ, represent the hydrogen atom, alkyl groups having no more than 4 carbon atoms, and the phenyl group; Q is an alkylene group having 1 to 7 carbon atoms or the phenylene group; and n is zero or an integer with a value of 1 through 4) is reacted with (b) a silane compound having the following formula (2)

$$Y^1SiR^3{}_a(OR^4)_{3-a}$$

(in formula (2), $Y^1$ is an alkyl group having a functional group reactive with the amino or imino moiety in the formula (1) amine compound, $R^3$ is an alkyl group, $R^4$ is an alkyl group or acyl group, and a equals zero, one, or two) to produce a reaction product having at least 1 amino or imino group in the molecule, and this reaction product is then reacted with (c) a functionalized carboxylic acid with the following formula (3)

$$Z^1—COOH$$

(in formula (3), $Z^1$ is a functional group reactive with the nitrogen atoms in the aforesaid reaction product) to produce (d) a compound with the following formula (4)

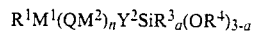

(in formula (4), $M^1$ and $M^2$, which may be the same or may differ, are groups selected from

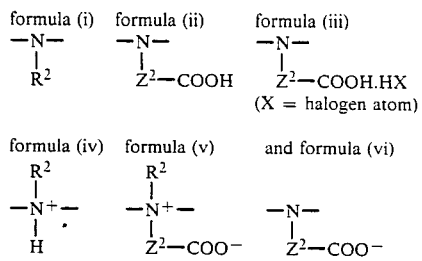

and at least one group selected from formulas (ii), (iii), (v), and (vi) is present in the molecule ($Z^2$ is the residue from the reaction between nitrogen and $Z^1$ in the formula (3) carboxylic acid described above, and a formula (vi) group is always present together with a formula (iv) group); $Y^2$ is the residue from the reaction of $Y^1$ in the above formula (2) silane compound with an amino or imino group; and $R^1$, $R^2$, Q, $R^3$, $R^4$, n and a are defined as above).

DETAILED DESCRIPTION OF THE INVENTION

In the present invention, the silyl group-containing amine compound having formula (4) is prepared by first reacting a specific amine compound (1) having formula (1) with a specific silane compound (2) having formula (2), and by subsequently subjecting the reaction product therefrom to a reaction with the specific carboxylic acid (3) having formula (3).

The Amine Compound (1)

The amine compound (1) used in the present invention has the following formula (1).

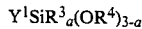

$R^1$ is exemplified by alkyl groups having 4 to 20 carbon atoms (e.g., butyl, octyl, lauryl, etc.), aryl groups, aralkyl groups (e.g., benzyl, chlorobenzyl, phenylbenzyl, diphenylmethyl, etc.), polyoxyalkylene (preferred examples consist principally of polyoxypropylene), moieties having the following formula; etc.

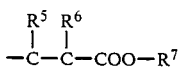

(In the preceding formula, $R^5$ and $R^6$ are each hydrogen or alkyl, and $R^7$=alkyl having 4 to 20 carbon atoms, aryl, aralkyl, polyoxylalkylene.)

One of these groups $R^2$ in formula (1) must be a hydrogen atom, while the other two groups $R^2$, which may be the same or may differ, are the hydrogen atom, alkyl groups having no more than 4 carbon atoms (e.g., methyl, ethyl, propyl, etc.), or the phenyl group. Furthermore, Q is an alkylene group having one to seven carbon atoms or the phenylene group, and n is zero or an integer with a value of 1 through 4.

These amine compounds (1) can be prepared by the reaction of a compound with the following formula

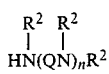

with a chloride or epoxy compound, acrylate, or methacrylate corresponding to the group $R^1$. Furthermore, various alkylamine compounds having 8 to 18 carbon atoms and the compound with the formula $$C_{18}H_{37}NHCH_2CH_2NH_2$$

are available commercially, among others.

For example, the use is preferred of amine compounds (1) obtained by the reaction of an alkyleneamine, for example, diethylenetriamine, etc., with compounds as expressed below.

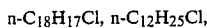

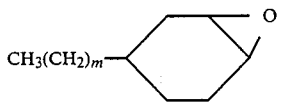

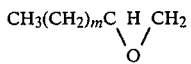

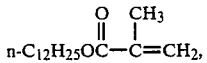

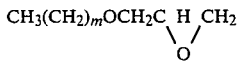

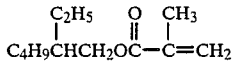

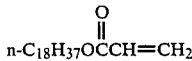

These reactions are known, and are conducted, for example, by the addition of excess alkyleneamine and heating to approximately 180 degrees Centigrade.

Examples of the amine compound (1) are as follows.

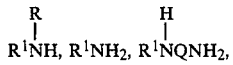

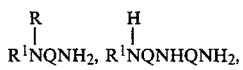

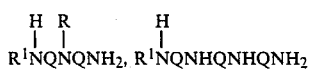

(In each formula, R is the phenyl group or an alkyl group having no more than 4 carbon atoms, $R^1$ and Q are defined as above, and $-CH_2CH_2-$ and $-CH_2CH_2CH_2-$ are preferred for Q.)

The Silane Compound (2)

The silane compound (2) used in the present invention is a silane compound which contains a functional group which will react with the amino or imino moiety in amine compound (1), and the former has the following formula (2).

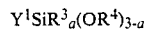

Here, $Y^1$ is a functional group which will react with the amino group ($-NH_2$) or the imino group ($>NH$), and it is concretely exemplified by the following.

$$ClCH_2CH_2CH_2-,$$

$$CH_2=C(CH_3)COOCH_2CH_2CH_2-$$

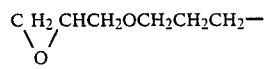

Furthermore, $R^3$ is an alkyl group having 1 to 4 carbon atoms, $R^4$ is an alkyl group or acyl group having 1 to 4 carbon atoms, and a is an integer with a value of zero to two. Preferred concrete examples of these are as follows: $-Si(OCH_3)_3$, $-SiCH_3(OCH_3)_2$, and $-Si(OCH_2CH_3)_3$.

With regard to the proportions of amine compound (1) and silane compound (2) in the aforesaid reaction, an excess of the amine compound (1) leads to a low yield, while an excess or large excess of silane compound (2) suppresses the subsequent reaction with the functionalized carboxylic acid (3) due to the reduction in nitrogen atoms available for reaction with the carboxylic acid's functional group. Consequently, a slight excess of silane compound (2) is preferred, for example, molar ratios of 1:ca. 1 through 1:ca. 1.5. In order to inhibit the reaction of the groups $-OR^4$ in silane compound (2), this reaction is advantageously conducted, for example, in an alcohol solvent at temperatures of 50 to 140 degrees Centigrade under a nitrogen blanket.

When, for example, the silane compound (2) has a group with the following formula,

hydrogen chloride will be produced as a by-product in this reaction. This hydrogen chloride is preferably neutralized using a suitable neutralization agent in order to make the next reaction with the carboxylic acid run smoothly. Concrete examples of said neutralization agent are sodium hydroxide; sodium alkylalcoholates having 1 to 4 carbon atoms; alkylamines such as ethylenediamine, diethylenetriamine, triethylenetetramine, etc.; other amines; and anion-exchange resins to which primary through quaternary amine is bonded. Furthermore, when sodium hydroxide is used as the neutralization agent, water is produced as a by-product, and it is preferably removed from the reaction system using a dehydrating agent such as silica gel, the various grades of molecular sieves, activated alumina, etc.

Through this reaction between amine compound (1) and silane compound (2), one obtains an amino-containing or imino-containing reaction product I, which is then reacted with the functionalized carboxylic acid (3) described in the following.

The Functionalized Carboxylic Acid (3)

The functionalized carboxylic acid (3) used in the present invention is a functionalized carboxylic acid which contains a functional group which will react with the primary, secondary, or tertiary nitrogen present in reaction product I, and it has the following formula (3).

$Z^1$—COOH

Concrete examples of this carboxylic acid (3) are carboxylic acid compounds having, for example, the following formula,

X—$R^8$—COOH (in the above formula, X—$R^8$ is a haloalkyl group, haloallyl group, haloaryl group, or haloaralkyl group, where the halogen is, for example, Cl, Br), as well as alpha,beta-unsaturated carboxylic acids, epoxy-containing alkylcarboxylic acids, etc. Actual examples are given below.

$ClCH_2COOH$, $ClCH_2CH_2COOH$, $CH_3CHClCOOH$, $CH_3CH=CHCOOH$, $CH_2=CH-CH=CHCOOH$,

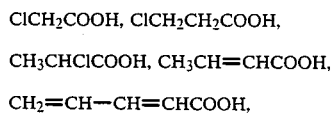

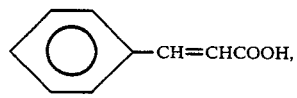

Furthermore, the functionalized carboxylic acid can also be used here as its alkyl ester, although a de-esterification must then be conducted after the reaction by hydrolysis using well known methods.

The proportion of carboxylic acid (3) to reaction product I in this reaction is not specifically restricted, and will depend on the proportion of nitrogen atoms in reaction product I onto which the functionalized carboxylic acid is to be introduced. In general, the reaction is preferably run using a molar ratio of about 1:1. Furthermore, the reaction can be run, for example, at room temperature or with heating.

The silyl group-containing amine compound with the following formula (4) is prepared as described above.

$R^1M^1(QM^2)_nY^2SiR^3{}_a(OR^4)_{3-a}$

In formula (4), $M^1$ and $M^2$, which may be the same or may differ, are groups selected from the following formulas (i) through (vi).

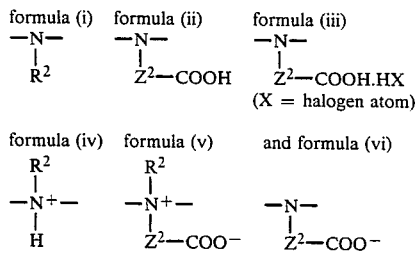

At least one group selected from formulas (ii), (iii), (v), and (vi) must be present in the molecule, and a formula (vi) group is always to be present together with a formula (iv) group. Here, $Z^2$ is the residue from the reaction between primary, secondary, or tertiary nitrogen and $Z^1$ in carboxylic acid (3); $Y^2$ is the residue from the reaction of $Y^1$ in the above formula (2) silane compound with an amino or imino group; and $R^1,R^2,Q,R^3,R^4$, n, and a are defined as above.

Using the method of the present invention, the target silyl group-containing amine compound is reliably prepared by first reacting the specific amine compound (1) with the specific silane compound (2), and by then reacting the reaction product I therefrom with the specific carboxylic acid (3).

Compared to this, if the amine compound (1) were to be preliminarily reacted with the carboxylic acid (3), a post-treatment would then be required, for example, arising from the necessity for protection of the carboxyl moiety of carboxylic acid (3) during the actual execution of the reaction.

As may be understood from formula (4), the silyl group-containing amine compound produced by the method of the present invention is a so-called carboxylic acid-type amphoteric surfactant, and more specifically is an amino acid-type or betaine-class carboxylic acid-type amphoteric surfactant. Accordingly, it has the properties and functions of typical amphoteric surfactants and can be used as such. In addition, the silyl group-containing amine compound under consideration, because it contains a silyl group in the molecule, can be attached to numerous substrates. Such substrates include glasses, natural and synthetic fibers, metals, various polymers, and so forth. Through its attachment to substrates in such a manner, it becomes suitable for use in new applications.

The present invention will be explained in the following using illustrative examples, but the invention is not limited to these examples.

The parameters for the high-performance liquid chromatography used in the examples were as follows.
  column: Shim-pack PREP-ODS (2×25 cm)
  solvent: methanol The parameters for nuclear magnetic resonance (NMR) absorption were as follows.
  frequency: 60 MHZ
  internal reference: TMS
  solvent: $CDCl_3$

EXAMPLE 1

Synthesis of the Amine Compound

4 Moles diethylenetriamine was placed in a four-neck flask and heated to 180 degrees Centigrade with stirring under a nitrogen current. To this was added dropwise 1 mol n-octyl chloride over 3.5 hours. After cooling, the diethylenetriamine hydrochloride product was separated. Distilling the transparent light-yellow liquid in vacuo at 123 to 135 degrees Centigrade and 1.5 mmHg afforded 200 g of a transparent, colorless fraction (1) (yield=93%).

The sharp absorption characteristic of primary amine in the vicinity of 1600 $cm^{-1}$ observed for diethylenetriamine was reduced in the infrared absorption spectrum of fraction (1). This fraction was subjected to high-performance liquid chromatography, and a peak having a retention time of 20.868 minutes was fractionated.

Analysis of this material by low-resolution NMR confirmed the presence of a total of 17 octyl protons: a three proton signal in the vicinity of 0.9 ppm (delta) for the terminal methyl group of the octyl group, and a 14 proton signal in the vicinity of 1.4 ppm (delta) for the 7 methylene groups in the octyl group. Furthermore, the 12 protons in the —NHCH$_2$CH$_2$NHCH$_2$CH$_2$NH$_2$ group were confirmed at 2.3 to 2.8 ppm (delta).

Based on the above findings, the obtained material was identified as an amine compound with the following chemical structure.

CH$_3$(CH$_2$)$_7$NHCH$_2$CH$_2$NHCH$_2$CH$_2$NH$_2$

Preparation of the Silyl Group-Containing Amine Compound 5.0 of fraction (1) prepared as above, 5.1 g gamma-chloropropyltrimethoxysilane, and 4.3 g methanol were sealed in a glass ampul, which was heated at 120 degrees Centigrade for 12 hours to produce a transparent yellow solution. After cooling, 9.3 g 10% methanolic sodium hydroxide and 14 g molecular sieve 3A (from Union-Showa Kabushiki Kaisha) were added and this was then stirred for 4 hours. The molecular sieve 3A and sodium chloride product were filtered off, the filtrate was concentrated to a nonvolatiles concentration of 90%, and the precipitated solid was again filtered off.

The primary amine absorption in the vicinity of 1600 cm$^{-1}$ observed for fraction (1) was not observed in the infrared absorption spectrum of this filtrate.

The filtrate was diluted with methanol to a nonvolatiles concentration of 45%. 10.6 g of this and 2.4 g of a methanol solution containing 50% monochloroacetic acid were sealed in a glass ampul, which was heated at 90 degrees Centigrade for 30 minutes to afford a transparent yellow solution. This liquid was subjected to high-performance liquid chromatography, and a peak having a retention time 17.5 minutes was fractionated.

This material was analyzed by low-resolution NMR, which comfirmed the presence of the 17 octyl group protons at 0.9 to 1.5 ppm (delta), the 9 trimethoxysilyl group protons in the vicinity of 3.4 ppm (delta), and the 2 methylene protons at the alpha-position on the carboxylic group in the vicinity of 4.8 ppm (delta). The molecular weight of this material was determined to be 485 by ebullioscopy in ethanol.

Based on the above findings, the chemical structure of the obtained material was identified as follows.

CH$_3$(CH$_2$)$_7$NHCH$_2$CH$_2$NCH$_2$CH$_2$NH(CH$_2$)$_3$Si≡(OCH$_3$)$_3$
|
CH$_2$—COOH.HCl

EXAMPLE 2

Synthesis of the Amine Compound

Triethylenetetramine was reacted with n-octyl chloride using the molar ratio and reaction conditions of Example 1, followed by separation of the triethylenetetramine hydrochloride. The resulting transparent yellow liquid was distilled in vacuo at 169 to 170 degrees Centigrade and 1.5 mmHg to afford a transparent colorless fraction (2).

The sharp primary amine absorption at 1600 cm$^{-1}$ observed for triethylenetetramine was weaker in the infrared absorption spectrum of fraction (2).

The chemical structure of fraction (2) was identified as follows.

CH$_3$(CH$_2$)$_7$NHCH$_2$CH$_2$NHCH$_2$CH$_2$NHCH$_2$Ch$_2$NH$_2$

Preparation of the Silyl Group-Containing Amine Compound 4.0 g of fraction (2) obtained as described above, 4.2 g gamma-methacryloxypropyltrimethoxysilane, and 1.7 g methanol were sealed in a glass ampul and then heated at 120 degrees Centigrade for 12 hours to afford a transparent brown solution.

The primary amine absorption in the vicinity of 1600 cm$^{-1}$ observed for fraction (2) was extinguished in the infrared absorption spectrum of this solution, but a broad secondary amine absorption remained. Furthermore, a sharp absorption in the vicinity of 1700 cm$^{-1}$ assigned to carbonyl appeared.

2.9 g of a methanol solution containing 50% monochloroacetic acid was added to this solution, and this was again sealed in a tube and then heated at 90 degrees Centigrade for 10 minutes to produce a thick, transparent brown liquid. This solution was subjected to high-performance liquid chromatography, and a peak with a retention time of 21.5 minutes was fractionated.

This material was analyzed by low-resolution NMR, which confirmed the following: the 17 octyl protons at 0.9 to 1.4 ppm (delta), the 9 trimethoxysilyl protons in the vicinity of 3.4 ppm (delta), and the 2 methylene protons at the alpha-position of the carboxyl group in the vicinity of 4.8 ppm (delta). The molecular weight of this material was determined to be 615 by ebullioscopy in ethanol.

Based on the above findings, the chemical structures in the obtained material were identified as follows.

CH$_3$(CH$_2$)$_7$NHCH$_2$CH$_2$NHCH$_2$CH$_2$NCH$_2$CH$_2$NH—
|
CH$_2$COOH.HCl

—CH$_2$CH(CH$_3$)—CO—O(CH$_2$)$_3$Si≡(OCH$_3$)$_3$ and

CH$_3$(CH$_2$)$_7$NHCH$_2$CH$_2$NCH$_2$CH$_2$NHCH$_2$CH$_2$NH—
|
CH$_2$COOH.HCl

—CH$_2$CH(CH$_3$)—CO—O(CH$_2$)$_3$Si≡(OCH$_3$)$_3$

EXAMPLE 3

Preparation of the Silyl Group-Containing Amine Compound 5.0 g fraction (2), 4.2 g gamma-chloropropyltrimethoxysilane, and 4.0 g methanol were sealed in a glass ampul and heated at 120 degrees Centigrade for 12 hours to prepare a transparent yellow solution.

To this solution were added 7.8 g 10% methanolic sodium hydroxide and 11.6 g molecular sieve 3A, followed by stirring for 4 hours. The molecular sieve 3A and sodium chloride product were filtered off, the filtrate was concentrated to a nonvolatiles concentration of 90%, and the precipitated solid was again filtered off.

The primary amine obsorption in the vicinity of 1600 cm$^{-1}$ observed for fraction (2) was extinguished in the infrared absorption spectrum of this filtrate.

The filtrate was diluted with methanol to a nonvolatiles concentration of 32.5%, and 12.0 g of this and 1.75 g of a methanol solution containing 50% monochloroacetic acid were sealed in a glass ampul and then heated at 90 degrees Centigrade for 30 minutes to afford a transparent yellow solution. This liquid was subjected to high-performance liquid chromatography, and a peak with a retention time of 19.15 minutes was fractionated.

This material was analyzed by low-resolution NMR, which comfirmed the following: the 17 octyl protons at 1.0 to 1.4 ppm (delta), the 9 trimethoxysilyl protons in the vicinity of 3.3 ppm (delta), and the 2 methylene protons at the alpha-position of the carboxyl group in the vicinity of 4.7 to 4.8 ppm (delta). The molecular weight of this material was determined to be 531 by ebullioscopy in ethanol.

Based on the above findings, the chemical structures in the obtained material were identified as follows.

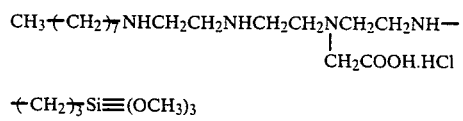

and

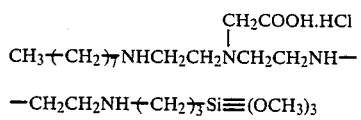

EXAMPLE 4

Synthesis of the Amine Compound

Diethylenetriamine and n-lauryl chloride were reacted using the molar ratio and reaction conditions described in Example 1, and the diethylenetriamine hydrochloride was then separated. Distilling the resulting transparent yellow liquid in vacuo at 168 to 169 degrees Centigrade and 2.0 mmHg afforded a transparent colorless fraction (3).

The sharp primary amine absorption at 1600 cm$^{-1}$ observed for diethylenetriamine was weakened in the infrared absorption spectrum for fraction (3).

The chemical structure of this fraction (3) was identified as follows.

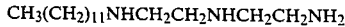

Preparation of the Silyl Group-Containing Amine Compound 5.0 g of fraction (3) prepared as above, 4.0 g gamma-chloropropyltrimethoxysilane, and 4.0 g methanol were sealed in a glass ampul and then heated at 120 degrees Centigrade for 12 hours to afford a transparent yellow solution.

After cooling, 11.1 g molecular sieve 3A and 7.4 g 10% methanolic sodium hydroxide were added to this solution, followed by stirring for 4 hours. The molecular sieve 3A and sodium chloride product were then filtered off, the filtrate was concentrated to a nonvolatiles concentration of 90%, and the precipitated solid was again filtered off.

The primary amine absorption in the vicinity of 1600 cm$^{-1}$ observed for fraction (3) was not present in the infrared absorption spectrum of this solution, while a broad secondary amine absorption did remain.

The filtrate was diluted with methanol to a nonvolatiles concentration of 32.7%, 12 g of this and 1.7 g of methanol solution containing 50% monochloroacetic acid were again sealed is in a glass ampul, and this was heated at 90 degrees Centigrade for 30 minutes to produce a tranparent yellow solution. This solution was subjected to high-performance liquid chromatography, and a peak with a retention time of 19.32 minutes was fractionated.

Analysis of this material by low-resolution NMR confirmed the following: the 25 lauryl group protons at 0.9 to 1.5 ppm (delta), the 9 trimethoxysilyl group protons in the vicinity of 3.3 ppm (delta), and the 2 methylene protons at the alpha-position of the carboxyl group in the vicinity of 4.8 ppm (delta). The molecular weight of this material was determined to be 538 according to ebullioscopy in ethanol.

Based on the above, the chemical structure of this material was identified as follows.

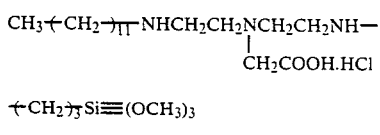

EXAMPLE 5

Synthesis of the Amine Compound

Iminobispropylamine and n-octyl chloride were reacted using the molar ratio and reaction conditions described in Example 1, and the iminobispropylamine hydrochloride was then separated. Distilling the resulting transparent yellow liquid in vacuo at 135 to 137 degrees Centigrade and 1.5 mmHg produced a transparent colorless fraction (4).

The sharp primary amine absorption at 1600 cm$^{-1}$ observed for iminobispropylamine was weakened in the infrared absorption spectrum of this fraction (4).

The chemical structure of the fraction (4) obtained as above was identified as follows.

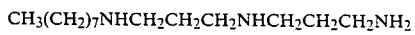

Preparation of the Silyl Group-Containing Amine Compound 5.0 g of the fraction (4) prepared as decribed above, 4.5 g gamma-chloropropyltrimethoxysilane, and 4.0 g methanol were sealed in a glass ampul and heated at 120 degrees Centigrade for 12 hours to afford a transparent yellow solution.

To this solution were added 8.2 g 10% methanolic sodium hydroxide and 12.4 g molecular sieve 3A, followed by stirring for 4 hours. The molecular sieve 3A and sodium chloride product were then filtered off, the filtrate was concentrated to a nonvolatiles concentration of 90%, and the precipitated solid was again filtered off.

The primary amine absorption in the vicinity of 1600 cm$^{-1}$ observed for fraction (4) was not present in the infrared absorption spectrum of this solution.

The filtrate was diluted with methanol to a nonvolatiles concentration of 35.2%, and 11 g of this and 1.8 g of a methanol solution containing 50% monochloroacetic acid were sealed in glass ampul and heated at 90 degrees Centrigrade for 30 minutes to prepare a transparent brown solution. This solution was subjected to high-perfomrance liquid chromatography, and a peak with a retention time of 21.32 minutes was fractionated.

Analysis of this material by low-resolution NMR confirmed the following: the 17 octyl protons at 0.9 to 1.4 ppm (delta), the 9 trimethoxysilyl protons in the vicinity of 3.4 ppm (delta), and the 2 methylene protons at the alpha-position of the carboxyl group in the vicinity of 4.8 to 4.9 ppm (delta). The molecular weight of this material was determined to be 513 by ebullioscopy in ethanol.

Based on these findings, the chemical structure of the obtained material was identified as follows.

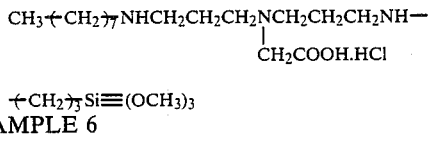

EXAMPLE 6

Preparation of the Silyl Group-Containing Amine Compound 5.0 g fraction (1), 5.1 g gamma-chloropropyltrimethoxysilane, and 4.3 g methanol were sealed in a glass ampul and heated at 120 degrees Centigrade for 12 hours to produce a transparent yellow solution.

After cooling, 9.3 g 10% methanolic sodium hydroxide and 14 g molecular sieve 3A were added to this solution, followed by stirring for 4 hours. The molecular sieve 3A and sodium chloride product were then filtered off, the filtrate was concentrated to a nonvolatiles concentration of 90%, and the precipitated solid was again filtered off.

The filtrate was diluted with methanol to a nonvolatiles concentration of 48%, and 10.8 g of this and 2.9 g of a methanol solution containing 40% monochloroacetic acid were sealed in glass ampul and heated at 90 degrees Centigrade for 1 hour to afford a transparent brown solution. This liquid was subjected to high-performance liquid chromatography, and a peak with a retention time of 18.25 minutes was fractionated.

Analysis of this material by low-resolution NMR confirmed the presence of the following: the 17 octyl group protons at 0.9 to 1.4 ppm (delta), the 9 trimethoxysilyl protons in the vicinity of 3.3 ppm (delta), and the 2 methylene protons at alpha-position of the carboxyl group in the vicinity of 4.9 ppm (delta). The molecular weight of this material was determined to be 483 by ebullioscopy in ethanol.

Based on the above findings, the chemical structure of the obtained material was identified as follows.

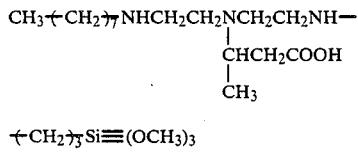

EXAMPLE 7

5.0 g laurylmethylamine, 5.5 g gamma-chloropropyltrimethoxysilane, and 4.5 g methanol were sealed in a glass ampul and heated at 120 degrees Centigrade for 16 hours in order to prepare a transparent yellow solution.

After cooling, 10 g 10% methanolic sodium hydroxide and 15 g molecular sieve 3A were added to this solution, followed by stirring for 4 hours. The molecular sieve 3A and sodium chloride product were filtered off, the filtrate was concentrated to a nonvolatiles concentration of 90%, and the precipitated solid was again filtered off.

The filtrate was diluted with methanol to a nonvolatiles concentration of 52%, and 10 g of this and 2.7 g of a methanol solution containing 50% monochloroacetic acid were sealed in a glass ampul and heated at 120 degrees Centigrade for 4 hours to prepare a transparent brown solution.

The chemical structure of the obtained material was identified as follows.

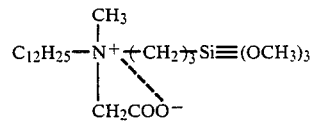

All of the silyl group-containing amine compounds sythesized in the preceding examples functioned as amphoteric surfactants.

That which is claimed is:

1. A method for the production of a silyl group-containing amine compound comprising reacting
   (a) a hydrocarbon-substituted amine compound having the formula

wherein $R^1$ is a monovalent hydrocarbon group; one of the three groups $R^2$ is a hydrocarbon atom while the other two, which are the same or differ, represent the hydrogen atom, alkyl groups having no more than 4 carbon atoms, and the phenyl group; Q is an alkylene group having 1 to 7 carbon atoms or the phenylene group; and n is zero or an integer with a value of 1 through 4, with (b) a silane compound having the formula

wherein $Y^1$ is an alkyl group having a functional group reactive with the amino or imino moiety in the amine compound, $R^3$ is an alkyl group, $R^4$ is an alkyl group or acyl group, and a equals zero, one, or two, resulting in a reaction product having at least 1 amino or imino group in the molecule, and reacting the reaction product with (c) a functionalized carboxylic acid with the formula $$Z^1\text{—COOH} \qquad (3)$$

wherein $Z^1$ is a functional group reactive with the nitrogen atoms in the reaction product, to produce said silyl group containing amine compound.

2. The method of claim 1 wherein $R^1$ is an alkyl group having 4 to 20 carbon atoms, an aryl group, aralkyl group, or a polyoxyalkylene moiety having the formula

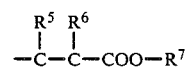

wherein $R^5$ and $R^6$ are each hydrogen or alkyl, and $R^7$=alkyl having 4 to 20 carbon atoms, aryl, aralkyl, or polyoxyalkylene.

3. The method of claim 2 wherein $Y^1$ is a radical selected from the group consisting of $ClCH_2CH_2CH_2-$ $CH_2=C(CH_3)COOCH_2CH_2CH_2-$, and $\underset{O}{CH_2\!-\!CHCH_2OCH_2CH_2CH_2-}$ 4. The method of claim 3 wherein the proportions of amine and silane reacted are in the molar ratios of 1:ca.1 to 1:ca.1.5.

5. The method of claim 4 wherein the reaction of amine and silane is conducted in an alcohol solvent under nitrogen, and at a temperature in the range of 50-140 degrees Centrigrade.

6. The method of claim 5 wherein the carboxylic acid has the formula $X-R^8-COOH$ wherein $R^8$ is alkyl, allyl, aryl, or aralkyl, and X is chlorine or bromine.

7. The method of claim 6 wherein the silyl group containing amine compound produced is a compound of the formula $R^1M^1(QM^2)_nY^2SiR^3{}_a(OR^4)_{3-a}$ wherein $M^1$ and $M^2$ are the same or differ, and are selected from the group consisting of radicals having the formulas

| formula (i) | formula (ii) | formula (iii) |
|---|---|---|
| $\begin{array}{c}-N-\\ \mid\\ R^2\end{array}$ | $\begin{array}{c}-N-\\ \mid\\ Z^2-COOH\end{array}$ | $\begin{array}{c}-N-\\ \mid\\ Z^2-COOH.HX\end{array}$ |
| formula (iv) | formula (v) | and formula (vi) |
| $\begin{array}{c}R^2\\ \mid\\ -N^+-\\ \mid\\ H\end{array}$ | $\begin{array}{c}R^2\\ \mid\\ -N^+-\\ \mid\\ Z^2-COO^-\end{array}$ | $\begin{array}{c}-N-\\ \mid\\ Z^2-COO^-\end{array}$ | and at least one group selected from formulas (ii), (iii), (v), and (vi) is present in the molecule, $Z^2$ is the residue from the reaction between nitrogen and $Z^1$ in the carboxylic acid, and a formula (vi) group is always present together with a formula (iv) group; $Y^2$ is the residue from the reaction of $Y^1$ in the silane compound with an amino or imino group; $R^1$, $R^2$, Q, $R^3$, $R^4$, n, and a are defined as above, and x is a halogen atom.

* * * * *